United States Patent [19]
Katzir et al.

[11] Patent Number: 5,450,201
[45] Date of Patent: Sep. 12, 1995

[54] APPARATUS AND METHOD FOR OPTICAL INSPECTION OF ARTICLES

[75] Inventors: Yigal Katzir, Rishon Lezion; Moshe Finarov, Rehovot, both of Israel

[73] Assignee: Orbotech Ltd., Yavne, Israel

[21] Appl. No.: 193,568

[22] Filed: Feb. 8, 1994

[30] Foreign Application Priority Data

Feb. 12, 1993 [IL] Israel .................................. 104708

[51] Int. Cl.⁶ ............................................ G01N 21/21
[52] U.S. Cl. ........................................... 356/369
[58] Field of Search ............... 356/364, 365, 366, 367, 356/368, 369, 381, 382, 371, 237; 250/225; 359/368, 371, 375, 386

[56] References Cited

U.S. PATENT DOCUMENTS

| | | | |
|---|---|---|---|
| 2,409,407 | 10/1946 | Turner | 359/371 |
| 3,614,195 | 10/1970 | Vollmer | 359/371 |
| 3,637,280 | 1/1972 | Beyer et al. | |
| 4,792,227 | 12/1988 | Yoshizawa | 356/128 |
| 4,866,264 | 9/1989 | Biricik et al. | 250/225 |
| 4,906,844 | 3/1990 | Hall | 250/225 |
| 4,999,014 | 3/1991 | Gold et al. | 356/369 |
| 5,042,951 | 8/1991 | Gold et al. | 356/381 |

FOREIGN PATENT DOCUMENTS

| | | |
|---|---|---|
| 4017935A1 | 6/1990 | Germany . |
| WO92/09880 | 6/1992 | WIPO . |
| WO92/0124-04 | 7/1992 | WIPO ............................ 356/369 |

OTHER PUBLICATIONS

IBM Technical Disclosure Bulletin, "Apparatus and Method for Film Thickness and Optical Constant Determination", vol. 31 No. 8, Jan. 1989, pp. 363–368.

Journal of Scientific Instrument, "Magneto-optic detection of ferromagnetic domains using vertical illumination"; vol. 39, No. 5, May 1962, pp. 244–245.

*Primary Examiner*—Hoa Q. Pham
*Attorney, Agent, or Firm*—Ladas & Parry

[57] ABSTRACT

Apparatus for optically inspecting an article, includes an illuminating system, an imaging system, and portable polarizing devices including a polarizer in the illuminating system, an analyzer in the imaging system, and a phase compensator in one of the systems. The illuminating system directs the light from the light source to the objective lens along an axis which is parallel to, but is laterally displaced from, the axis of the objective lens, such as to illuminate the inspected article with a cone of light which is tilted at an angle relative to the axis of the objective lens to thereby permit contrast enhancement of the illuminated inspected article by the null-ellipsometric effect.

20 Claims, 5 Drawing Sheets

APPARATUS AND METHOD FOR OPTICAL INSPECTION OF ARTICLES

FIELD AND BACKGROUND OF THE OPERATION

The present invention relates to apparatus, and also to a method, for optically inspecting articles in order to obtain maximum contrast. The invention is particularly applicable for use in optical microscopes, in order to enhance the contrast between different materials or layers in the inspected articles, and the invention is therefore described below with respect to such an application.

The optical microscope is a well known and widely used instrument for observing small objects and minute details of surfaces in a wide variety of fields. It is particularly useful for visual inspection of electronic products, such as integrated circuits, multi-chip modules, flat panel displays, and the like, all characterized by finely detailed surfaces.

Several well known contrast enhancing techniques in microscopy use polarizers in the optical path. Accordingly, most commercially available microscopes may be equipped with a polarizer in the illuminating system, and an analyzer in the imaging system, with the polarizer rotatable around the illumination axis so that the orientation of the polarization axis is continuously variable within an angular range of about 90°. Such microscope illuminating systems may also include a phase compensator, or a phase retardation plate, which introduces a phase shift of 360° between the s- and p- polarization components.

However, some important types of articles or workpieces are hard to inspect with the prior art microscopes because the known contrast enhancement techniques fail to yield adequate contrast. One type of such article is a glass substrate coated with an indium-tin oxide (ITO) patterned layer about 100 nm thick, overcoated with a polyimide (PI) film about 80 nm thick, which is used in liquid crystal displays (LCD). These articles should be inspected particularly for regions of possible absence of the polyimide film. However, no microscopic technique is known to the inventors which adequately differentiates between regions coated with such a thin layer, and uncoated regions.

Another example of hard-to-inspect articles is silicon coated with a silicon dioxide layer of less than 50 $\mu$m thickness, a common stage in the fabrication of microelectronic devices. However, the known microscopic techniques are unable to provide adequate contrast for examining the silicon dioxide layer.

There is therefore a critical need for optical inspection apparatus which and method which enhance the contrast between different materials in the article even when extremely thin layers or films are involved.

OBJECTS AND BRIEF SUMMARY OF THE INVENTION

According to the present invention, there is provided apparatus for optically inspecting an article, comprising: an illuminating system including a light source for illuminating the inspected article via an objective lens; an imaging system for receiving the light from the inspected article; and polarizing devices including a polarizer in the illuminating system, an analyzer in the imaging system, and a phase compensator in one of the systems, the polarizing devices being rotatable about their respective axes; characterized in that the illuminating system includes light directing means for directing the light from the light source to the objective lens along an axis which is parallel to, but is laterally displaced from, the axis of the objective lens, such as to illuminate the inspected article with a cone of light which is tilted at an angle relative to the axis of the objective lens to thereby permit contrast enhancement of the illuminated inspected article by the null-ellipsometric effect.

The null-ellipsometric effect referred to above is more particularly described in U.S. Pat. No. 5,333,052, assigned to the same assignee as the present application, which patent is hereby incorporated by reference. Briefly, this effect is produced when two of the above three polarization devices are selectively rotated about their respective axes while maintaining the third device stationary. At some position, the reflected light will be "extinguished" with respect to one of the materials, thereby maximizing the contrast between the two (or more) materials on the article being inspected.

The present invention exploits the null-ellipsometric effect to enhance contrast in a microscope. As set forth above, this is done by directing the light to the microscope objective lens along an axis which is parallel to, but is laterally displaced from, the axis of the objective lens, such as to illuminate the workpiece with a cone of light Which is tilted at an angle relative to the axis of the objective lens.

According to further features in the preferred embodiment of the invention described below, the light directing means includes a variable stop in the illuminating system forwardly of the objective lens, which stop is adjustable to vary the lateral displacement of the light with respect to the axis of the objective lens, and thereby the contrast enhancement by the null-ellipsometric effect. In the described preferred embodiment, the diameter of the variable stop is also adjustable.

In the conventional microscope the phase compensator, sometimes called a phase retardation plate, generally introduces a phase shift of 360°. In the preferred embodiment of the invention described below, the phase compensator is a quarter-wave plate.

According to further features in the preferred embodiment of the invention described below, the illuminating system includes a mode selector device for selecting either a Normal mode wherein the phase compensator is moved out of the axis of the illuminating system, or a Variable Contrast mode wherein the phase compensator is moved into the axis of the illuminating system. In the described preferred embodiment, the mode selector device includes a slidable plate having a first opening which is moved into the axis of the illuminating system in the Normal mode, and a second opening occupied by the phase compensator which is moved into the axis of the illuminating system in the Variable Contrast mode; the phase compensator is rotatable about its axis to vary the contrast in the latter mode.

According to a further aspect of the invention, there is provided a method of using the above-described apparatus for optically inspecting an article to obtain maximum contrast of the image.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF A PREFERRED EMBODIMENT

Figure 1:
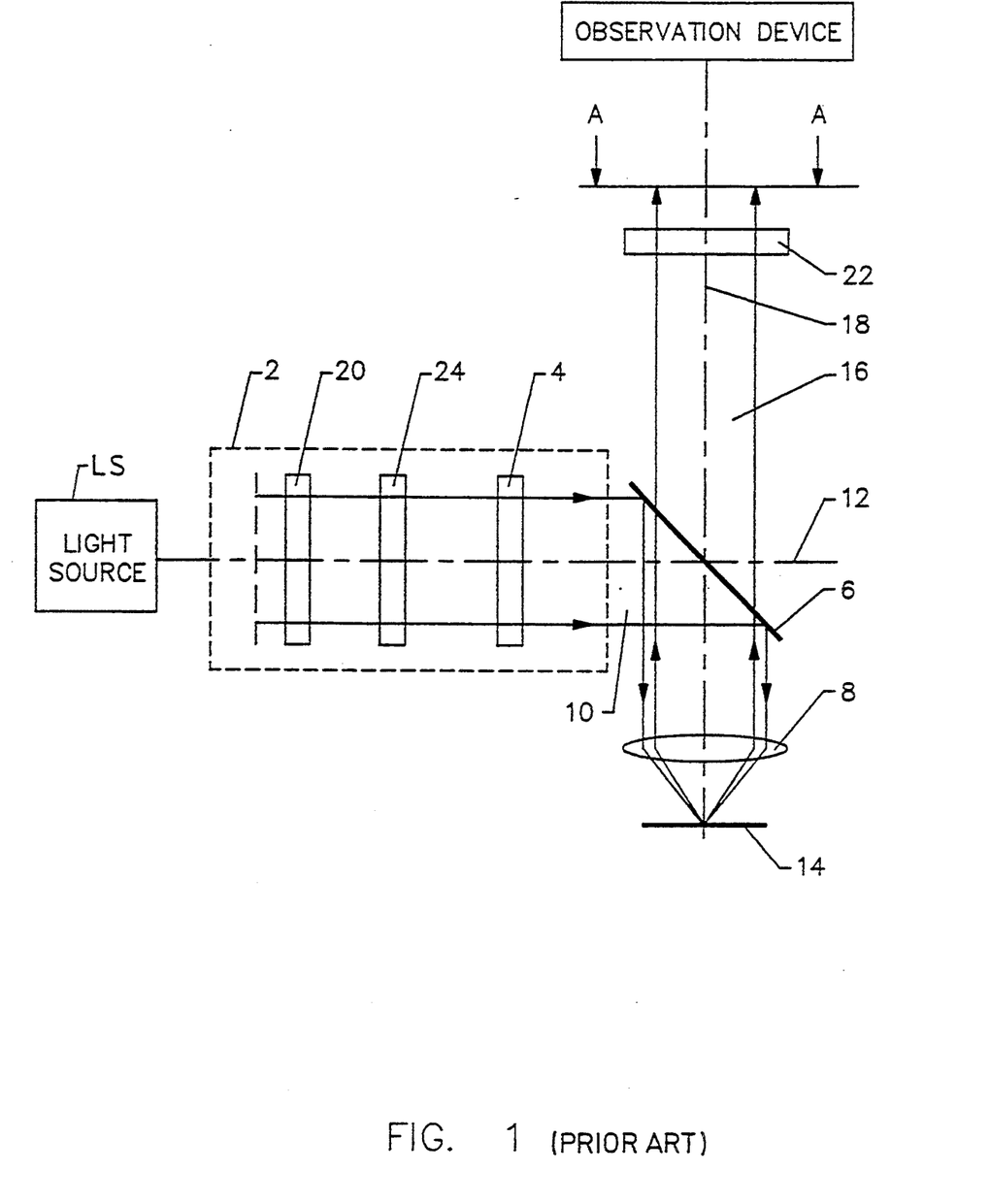
FIG. 1 schematically illustrates a conventional (prior art) microscopic apparatus for optically inspecting an article.

With reference first to FIG. 1, there is schematically illustrated the optical system of a standard incident light microscope, such as the Ergolux made by Leica Wetzlar. This microscope includes an illuminating system comprising a light source LS, a Kohler illuminator 2 which includes a variable aperture stop 4, a beam splitter 6, and an objective lens 8. During bright field illumination, the illuminator 2 provides a light beam 10 along the illumination axis 12. The light beam passes through the aperture stop 4, is then reflected by the beam-splitter 6, and is finally focussed by the objective lens 8 to illuminate the inspected surface 14 of the article being inspected.

The same objective lens 8 collects the light relected from surface 14 and forms the image beam 16 along the imaging axis 18. The image beam passes through the beam splitter 6 and is directed towards the observation device above the line A—A, such as a binocular tube MS.

As indicated earlier, such known microscopes provide contrast enhancement by the use of polarizers in the optical path. Accordingly, most commercially available microscopes may be equipped with a polarizer 20 in the illuminator 2, and an analyzer 22 in the imaging system. In addition, the polarizer 20 may be rotated around the illumination axis 12 so that the orientation of its polarization axis is continuously variable within an angular range of about 90°. Such a microscope illuminator may additionally include a phase compensator 24, such as a phase retardation plate which introduces a phase shift of 360° between the s- and p- polarization components.

However, as was also indicated earlier, such a conventional microscope inspection apparatus is not capable of adequately differentiating between regions coated with extremely thin layers and uncoated regions. The present invention modifies the conventional microscope inspection apparatus in order to enhance contrast by exploiting the null-ellipsometric effect.

Figure 2:
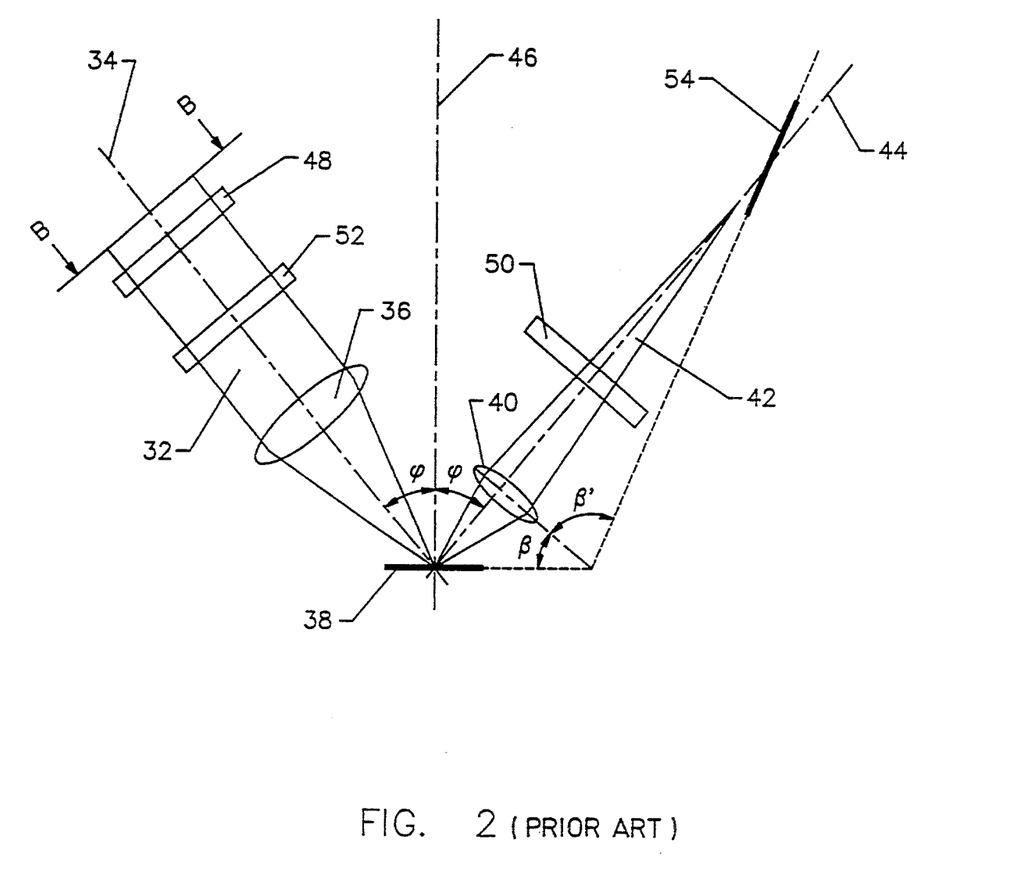
FIG. 2 schematically illustrates the null-ellipsometric effect, as described for example in the above-cited U.S. Pat. No. 5,333,052.

The null-ellipsometric effect is described more particularly in our above-cited U.S. Pat. No. 5,333,052, and is schematically shown in FIG. 2 of the accompanying drawings. As shown in FIG. 2, the illuminator, located beyond the B—B line, provides a light beam 32 along the illumination axis 34, which is focussed by the condenser lens 36 on the workpiece 38. The objective lens 40 projects the imaging beam 42 along the imaging axis 44. The angle of incidence $\phi$ between the normal 46 to the workpiece surface and the illumination axis 34 is preferably slightly less than the Brewster angle of the substrate, e.g., 50° when the substrate is a glass plate. Obviously, the angle of reflection is equal to the angle of incidence.

The apparatus illustrated in FIG. 2 further includes a polarizer 48 in the illumination system, and an analyzer 50 in the imaging system. It further includes a phase compensator 52, in the form of a quarter-wave plate; in this case, the phase compensator 52 is in the illuminating system, but it could be in the imaging system. The polarizer 48 and the analyzer 50 are rotatable around their respective optical axes. By rotating the polarizer 48 and the analyzer 50, each one in turn, it is possible to extinguish the light beam reflected from a portion of the workpiece corresponding to one material on the workpiece, while other regions of the workpiece composed of other materials remain relatively bright. This is the null-ellipsometric effect which permits the contrast to be enhanced, as described in our above-cited U.S. Pat. No. 5,333,052.

While the above-described null-ellipsometric technique is highly useful for automated inspection using a line sensor, its use for visual observation (e.g., via a microscope) is hampered by the fact that the image plane 54 of the objective lens 40 is tilted relative to the imaging axis 44 by a certain angle which is calculated according to the Scheimpflug relation:

$$\tan \beta' = M \cdot \tan \beta.$$

For example, for $\phi = 50°$, $M = 20X$, the tilt angle $\beta'$ should be 87.6°.

Obviously, at such grazing angles it would be impractical to obtain good image quality over a reasonable field of view. If, for example, such conventional imaging devices as an area CCD camera is used, only a small part of its light sensitive area may be located in focus. At the high optical magnifications employed in the inspection of microelectronic products, the tilt angle $\beta'$ approaches grazing conditions very quickly.

Figure 3:
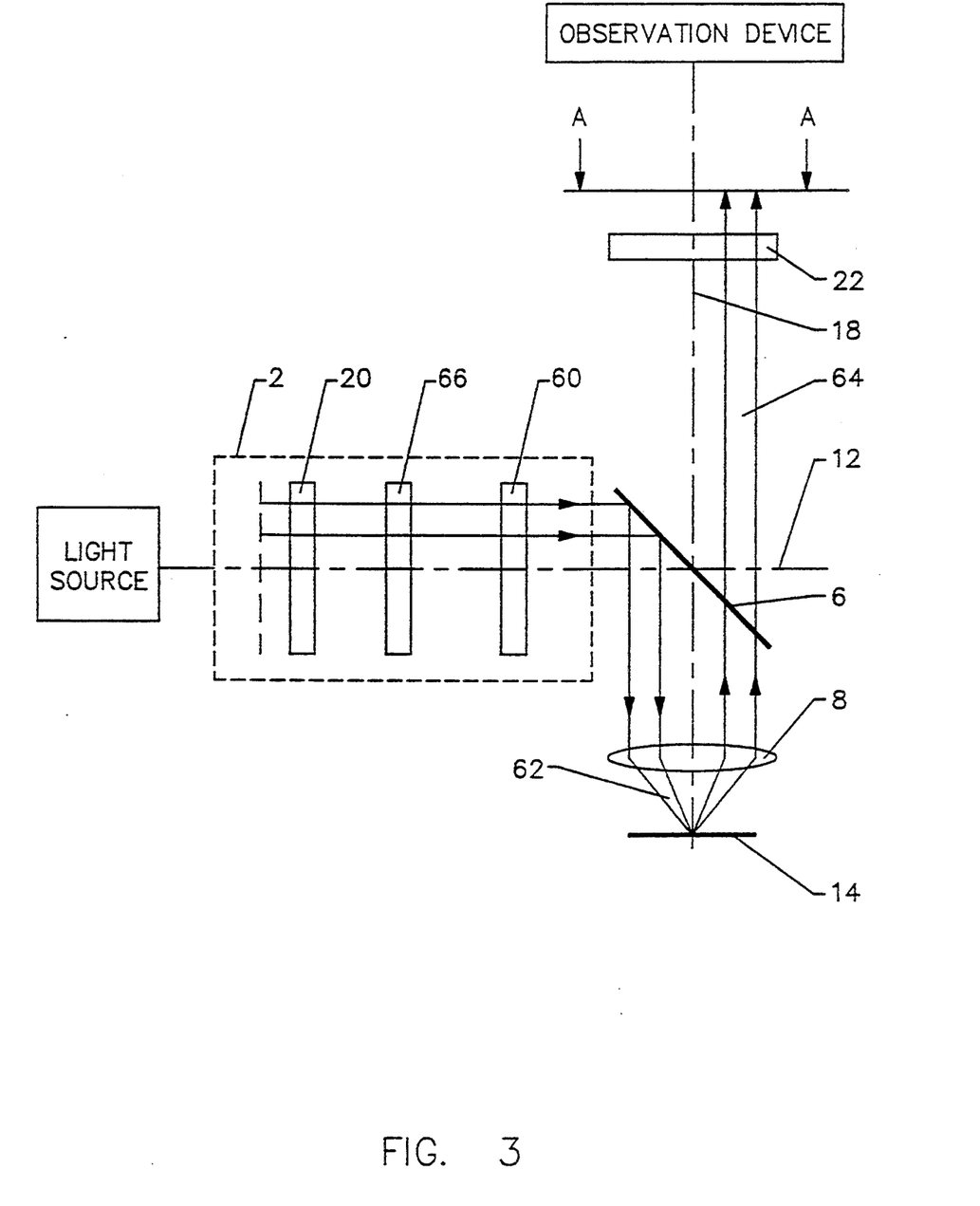
FIG. 3 is a diagram schematically illustrating one form of apparatus constructed in accordance with the present invention for obtaining contrast enhancement by the null-ellipsometric effect.

FIG. 3 schematically illustrates one form of apparatus constructed in accordance with the present invention to provide an optical microscope with a contrast enhancing capability based on the null-ellipsometric effect. To facilitate understanding of the apparatus of FIG. 3, those parts which are the same as in the conventional microscopic inspection apparatus illustrated in FIG. 1 are identified by the same reference numerals, and therefore the description below will concentrate mostly on the changes in the conventional microscope apparatus to provide contrast enhancement by the null-ellipsometric effect.

One important difference in the conventional microscope inspection apparatus is that the illuminating system includes light-directing means for directing light from the light source LS to the objective lens 8 along an axis which is parallel to, but is laterally displaced from, the axis 18 of the objective lens, such as to illuminate the workpiece 14 with a cone of light which is tilted at an angle relative to the axis 18 of the objective lens. For this purpose, in FIG. 3, the variable aperture stop, designated 60 in FIG. 3, is placed off-center with respect to the illumination axis 12. As a result, the workpiece is illuminated by a light cone 62 which is tilted relative to the imaging optical axis 18. Since optical axis 18 is perpendicular to the workpiece surface, the reflected image-forming beam 64 is likewise tilted relative to the surface. Therefore, this optical scheme provides the necessary condition for implementing the "ellipsometric imaging" and contrast enhancement by null-ellipsometric effect.

This contrast enhancement technique requires objective lenses of very high Numerical Aperture (NA). For example, for glass substrates a minimum NA of 0.8 is preferred, whereas for silicon substrates a minimum NA of 0.9 is preferred. This would enable the tilt angle of the light cone to approach the Brewster angle for the respective substrate.

The diameter of the stop 60 also affects the imaging properties of the apparatus: a smaller diameter tends to enhance the ellipsometric effect, thereby improving the contrast. At the same time, however, it leads to decreased light level and increased spatial coherence, which adversely affect the image quality. Therefore a variable aperture stop is used permitting such parameters as the stop diameter and the displacement of its center from the illumination axis, to be varied and optimized for the particular objective lens and type of inspected workpiece.

Another change in the conventional microscope inspection apparatus included in the apparatus of FIG. 3 is that the phase compensator, therein designated 66 (sometimes referred to as a phase retardation plate) is a quarter wave ($\tau/4$) plate. Since in most applications it is anticipated that "white" (spectrally wide band) light will be used, this compensator should desirably be achromatic; i.e., it provides nearly the same phasse shift for any wavelength within a broad spectral range. An example of an available phase compensator is the Achromatic Quarter Wave Retarder of Meadowlark Optics company, which employs several layers of birefringent polymer materials.

While the phase compensator 66 is shown in FIG. 3 as inside the illumination path of the microscope, it may also be placed in the imaging path, between the objective lens 8 and the analyzer 22, if it is more convenient to do so in a particular application.

At least two out of three polarizing components (20, 22, 66) should be rotatable around the corresponding optical axis (12 or 18), such that the orientation of their polarization axes relative to the plane of incidence (the plane of the drawing in FIG. 3) may be varied at will. Accordingly, there are three possible configurations: (1) the analyzer is fixed, preferably at an azimuth of ±45°, and the compensator and polarizer are rotatable; (2) the polarizer is fixed, preferably at an azimuth of ±45°, and the analyzer and compensator are rotatable; and (3) the compensator is fixed, preferably at an azimuth of ±45°, and the analyzer and polarizer are rotatable.

All three configurations are equivalent from a performance standpoint. For reasons of convenience, however, configuration (1) is preferable because the necessary rotation mechanism is easier to incorporate inside the illuminator module of the microscope. An example for a commercial microscope that readily lends itself to such modification is the Ergolux made by Leica Wetzlar.

The apparatus illustrated in FIG. 3 may be operated as follows:

1. The operator begins by setting up the microscope for the bright field incident illumination mode, hereinafter called the Normal mode. The operator then selects the appropriate objective lens and observation device (e.g., a binocular tube, a video camera connected to a TV monitor, etc.).

2. The operator then sets the rotatable polarization components to their initial positions, i.e., all three components at the same azimuth of 45°; this setting is the closest one to a normal microscopic observation.

3. Setting the microscope to the Variable Contrast mode is now performed by (a) shifting the aperture stop off the center position and (b) decreasing its diameter below the usual setting for ordinary microscopy. As a first iteration, the aperture stop may be centered around the middle of the radius of the full aperture, its diameter decreased to half that of the full aperture; and then the stop shifted laterally off its center position. When working with binocular system, these steps may be visually monitored by removing one eyepiece and looking directly through the eyepiece tube.

4. The polarizer 20 and the phase compensator 66 are then sequentially rotated, one after the other, to vary the contrast of the image up to full "extinction" of certain features.

5. If the contrast obtained after several iterations is still unsatisfactory, the contrast may still be improved by further shifting and reducing the aperture stop 60.

Figure 4A:
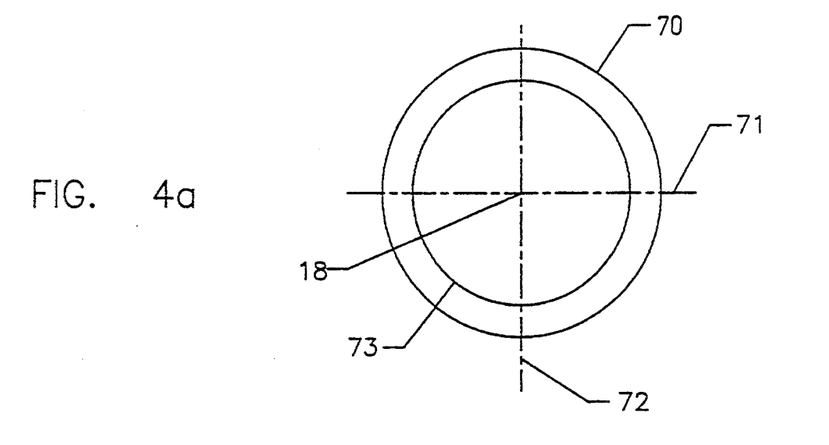
FIGS. 4a–4c illustrate the positions of a variable aperture stop in the apparatus of FIG. 3 during a setup procedure.
Figure 4B:
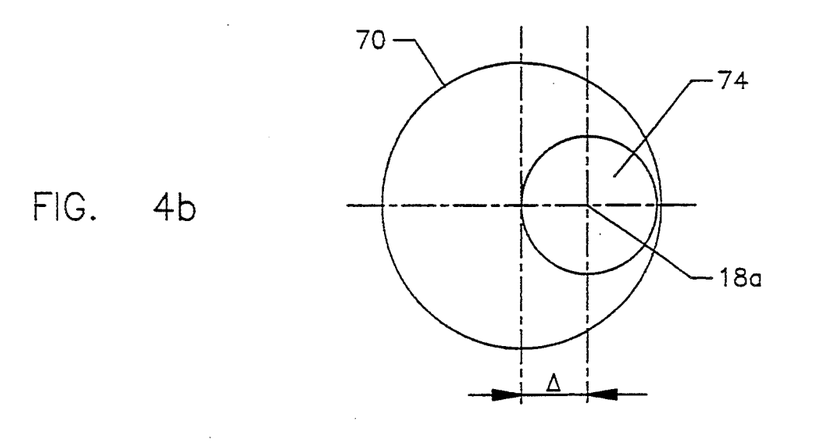
Figure 4C:
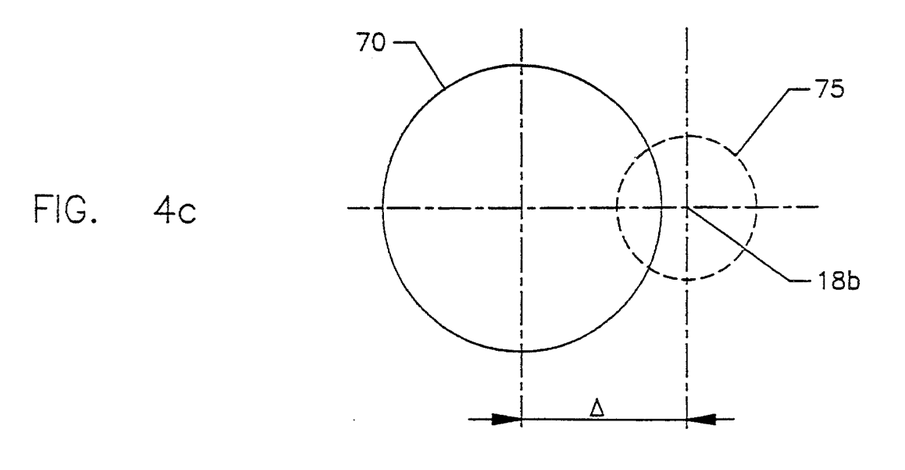

The latter operations are more particularly illustrated in FIGS. 4a-4c.

FIG. 4a shows a typical setting in prior art microscopy, which would be the case in the Normal mode of operation of the apparatus illustrated in FIG. 3. In this typical setting, circle 70 denotes the full aperture of the objective lens 8 in the plane of the aperture stop 60. The aperture, designated 73, is usually set so that its diameter is about two-thirds of the clear aperture 70. Both apertures are concentric and centered around the optical axis of the microscope, indicated at 18 in FIG. 4a, which is the intersection of the X, Y-axes of the device, shown at 71 and 72, respectively.

FIG. 4b shows the preferred first iteration of the variable aperture stop 60 in FIG. 3. The diameter of the aperture, shown at 74, is reduced to about one-half that of the clear aperture 70, and its center is displaced to about the middle of the clear aperture, as shown by axis 18a in FIG. 4b. This displacement relative to the microscope optical axis (18, FIG. 4a) is denoted "Δ" in FIG. 4b.

FIG. 4c illustrates an extreme situation in the shifting and reducing of the aperature stop, therein designated 75, if several iterations as described above with respect to FIG. 4b are still unsatisfactory. In the extreme situation illustrated in FIG. 4c, the aperture 75 is very small and is displaced so that its center 18b is outside of the clear aperture 70. This case may be useful for ellipsometric contrast enhancement, but is undesirable from a light intensity and spatial resolution standpoint.

Figure 5:
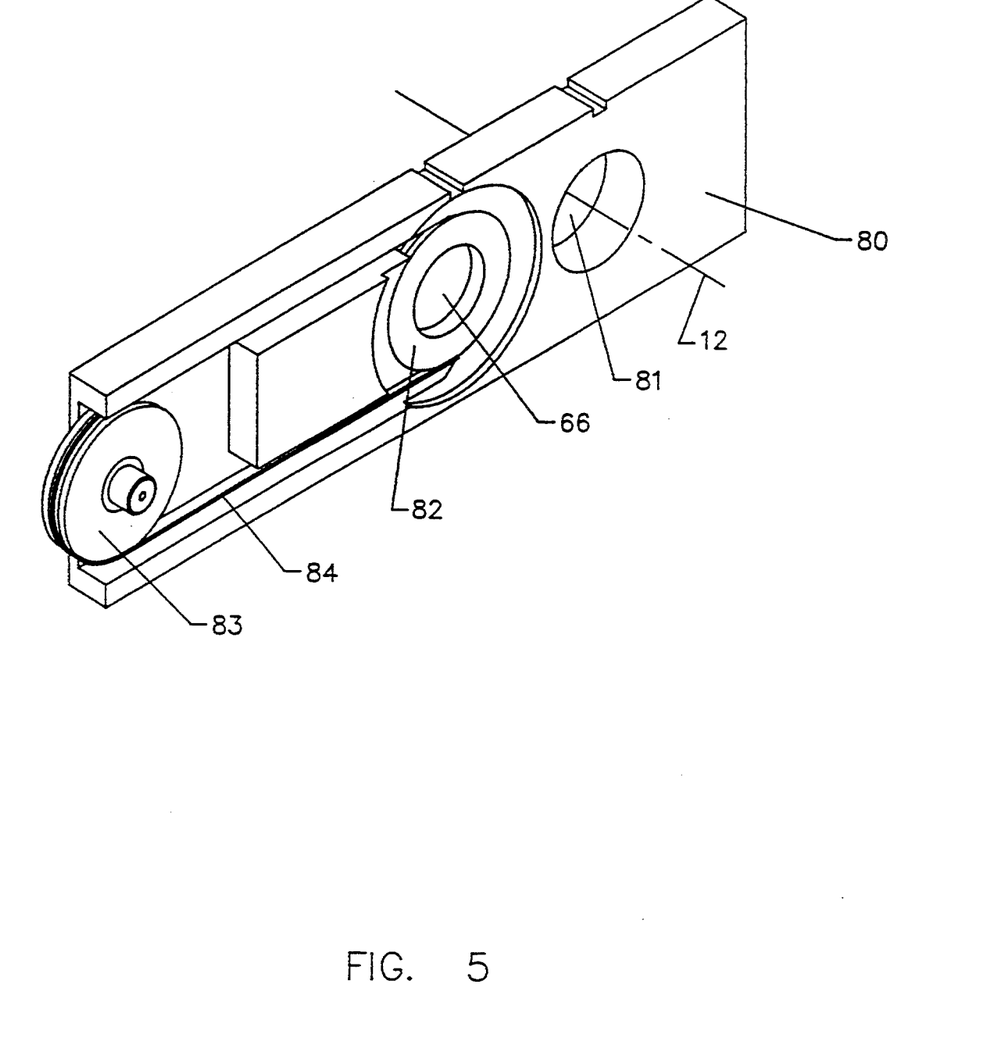
FIG. 5 illustrates one form of mode selector device which may be used in the apparatus of FIG. 3 for selecting either a Normal mode or a Variable Contrast mode of operation.

FIG. 5 illustrates how the contrast enhancement technique of the present invention may be implemented in standard optical microscopes with minimum design changes. Illustrated in FIG. 5 is a phase compensator slider, generally designated 80, included in the Leica Ergolux microscope but modified to permit that microscope to be operated according to the Normal mode, or to a Variable Contrast mode in accordance with the present invention. Thus, slider 80 may be positioned in the microscope illuminator (2 in FIGS. 1 or 3) at two interchangeable positions, one for the Normal mode of operation, and the other for the Variable Contrast mode of operation, as selected by the operator.

For this purpose, slider 80 is formed with an empty clear aperture 81 to be placed in alignment with the illumination optical axis (12 in FIGS. 1 and 3) during the Normal mode of operation.

Slider 80 is formed with a second aperture which includes a hollow rotatable shaft 82 occupied by the phase compensator 66. In order to condition the apparatus for the Variable Contrast mode of operation, slider 80 is moved to align the phase compensator 66 with the illumination optical axis 12. The phase compensator 66 may be rotated by a pulley wheel 83 projecting through an opening at one end of the slider to enable it to be manually rotated, and a pulley belt 84 coupling the hollow shaft 82 to the pulley wheel.

It will thus be seen that the microscopic contrast enhancement apparatus and method described above provide a new and powerful tool in the field of optical inspection. The main advantages in this technique over the prior standard microscopic art techniques include the following:

1. Very high contrast may be obtained with the null-ellipsometric effect in situations where prior art microscopic techniques yield only poor contrast. Common examples are workpeices composed of Glass-ITO-PI or Silicon-Silicon Dioxide structures. The new technique therefore can significantly expand the range of workpiece types that may be inspected with standard microscopes.

2. The contrast between different portions of workpieces, e.g., between two different multilayer structures, may be varied over a wide range. Typically, contrast reversal is observed between extreme settings, i.e., an area that appears relatively dark in one setting becomes relatively bright in another setting of the polarizing components. The variable contrast property makes the foregoing technique ideally suitable for defect classification in the field of visual inspection. Thus, the origin of a suspected defect may be traced according to its contrast variation properties relative to neighboring known structures. For instance, suppose a small unknown island defect in an area that should have been clean silicon, changes its contrast the same manner as the proper silicon dioxide layer in other areas. This would readily identify the defect as a superfluous spot of silicon dioxide.

3. High sensitivity of null-ellipsometric contrast to a thickness of thin transparent films enables to inspect, with this microscope, thickness non-uniformity of different layers, both single and in multilayer structures. For example, if the image of a certain point of an inspected film is dark ("extinguished"), other points with the same film thickness will be also dark, while the areas with different thicknesses will be bright, under the same conditions. Thus a gray level in the image is a function of the thickness difference between the inspected and reference points, and may be used for thickness non-uniformity inspection. Sensitivity of such an inspection depends on the NA of the objective, displacement and dimension of the aperture stop (which together determine the angle of incidence of the illumination light cone and its angular width), as well as on the spectral band width of the used light, and may reach single nanometers in optimal conditions.

4. The invention may be easily implemented on a standard optical microscope (e.g., the prior art microscope illustrated in FIG. 1) by merely exchanging the phase compensator plate (24, FIG. 1) for a slider plate as illustrated in FIG. 5, and making the relatively minor mechanical modifications to enable rotating the polarizer and the compensator, and to enable decreasing the diameter of the aperture (60, FIG. 3) and displacing it laterally of the axis of the objective lens as described above.

With the preferred Leica Ergolux microscope no modification of the aperture 60 is necessary, as this microscope is already equipped with an aperture slider. Originally designed to change the illumination mode between bright field and dark field in its extreme positions, the slider may also be manually moved in small increments for effecting the Variable Contrast mode. However, it is anticipated that practical embodiments of the invention will include a more precise mechanism, whether manual or motorized, for controlling the size and displacement of the aperture.

While the invention has been described with respect to one preferred embodiment, it will be appreciated that this is set forth merely for purposes of example, and that many other variations, modifications and applications of the invention may be made.

What is claimed is:

1. Apparatus for optically inspecting an article in a manner permitting enhancement of contrast between different materials in the article, comprising:

an illuminating system including a light source for illuminating the inspected article via an objective lens having an axis;

an imaging system for receiving the light from the inspected article;

and polarizing devices including a polarizer in said illuminating system, an analyzer in said imaging system, and a phase compensator in one of said systems, each of at least two of said polarizing devices having an axis of rotation and being rotatable about its respective axis of rotation;

characterized in that said illuminating system includes light directing means for directing the light from said light source to said objective lens along an axis which is parallel to, but is laterally displaced from, the axis of the objective lens, such as to illuminate each point of the inspected article with a cone of light which is tilted at an angle relative to the axis of the objective lens to thereby permit contrast enhancement between different materials in the image of the illuminated inspected article by the null-ellipsometric effect.

2. The apparatus according to claim 1, wherein said light directing means includes a variable stop in the illuminating system forwardly of the objective lens, which stop is adjustable to vary the lateral displacement of the light with respect to the axis of the objective lens, and thereby said contrast enhancement by the null-ellipsometric effect.

3. The apparatus according to claim 2, wherein said stop is a variable aperture stop whose diameter is also adjustable.

4. The apparatus according to claim 2, wherein said illuminating system includes a beam splitter for reflecting the light from said variable aperture stop via said objective lens to the inspected article, and for transmitting the light from the inspected article via said objective lens to the imaging system.

5. The apparatus according to claim 1, wherein said phase compensator is a quarter-wave plate.

6. The apparatus according to claim 5, wherein said light source produces a spectrally wide band of light, and said phase compensator is achromatic.

7. The apparatus according to claim 1, wherein said objective lens has a Numerical Aperture of at least 0.8

8. The apparatus according to claim 1, wherein said phase compensator is in the illuminating system between the polarizer and the objective lens.

9. The apparatus according to claim 8, wherein said illuminating system includes a mode selector device for selecting either a Normal mode wherein said phase compensator is moved out of the axis of the illuminating system, or a Variable Contrast mode wherein said phase compensator is moved into the axis of the illuminating system.

10. The apparatus according to claim 9, wherein said selector device includes a slidable plate having a first opening which is moved into the axis of the illuminating system in the Normal mode, and a second opening occupied by the phase compensator which is moved into the axis of the illuminating system in the Variable Contrast mode, said phase compensator being rotatable about its axis to vary the contrast in said latter mode.

11. The apparatus according to claim 10, wherein said phase compensator is mounted in a hollow shaft which is rotatable about its axis.

12. The apparatus according to claim 11, wherein said hollow shaft is rotatable by a pulley wheel carried by said slidable plate and coupled to said hollow shaft by a pulley belt.

13. The apparatus according to claim 1, wherein said imaging system includes a binocular tube.

14. A method for optically inspecting an article in a manner enhancing the contrast between different materials in the article by optical apparatus, comprising:
an illuminating system including a light source for illuminating the inspected article via an objective lens having an axis;
an imaging system for receiving the light from the inspected article;
and polarizing devices including a polarizer in said illuminating system, an analyzer in said imaging system, and a phase compensator in one of said systems, each of at least two of said polarizing devices having an axis of rotation and being rotatable about its respective axis of rotation;
characterized in directing the light from said light source to said objective lens along an axis which is parallel to, but is laterally displaced from, the axis of the objective lens, such as to illuminate each point of the inspected article with a cone of light which is tilted at an angle relative to the axis of the objective lens to thereby enhance contrast between different materials in the image of the illuminated inspected article by the null-ellipsometric effect.

15. The method according to claim 14, including varying, by means of a variable aperture stop, the lateral displacement of the light with respect to the axis of the objective lens in order to obtain maximum contrast between the different materials in the image of the inspected article.

16. The method according to claim 15, including varying the diameter of the variable aperture stop in order to obtain maximum contrast between the different materials in the image of the inspected article.

17. The method according to claim 16, wherein obtaining said maximum contrast is effected by:
initially setting all the polarizing devices to the same azimuth position of 45°;
shifting the aperture stop laterally of the axis of the objective lens;
decreasing the diameter of the aperture stop below the usual setting for ordinary microscopy;
and rotating the polarizer and phase compensator sequentially, one after the other, to obtain maximum contrast of the image.

18. The method according to claim 14, wherein said phase compensator is a quarter-wave plate.

19. The method according to claim 14, wherein said light source produces a spectrally wide band of light, and said phase compensator is acromatic.

20. The method according to claim 14, wherein said objetive lens has a Numerical Aperture of at least 0.8.

* * * * *